United States Patent [19]
Serbousek et al.

[11] Patent Number: 6,066,142
[45] Date of Patent: May 23, 2000

[54] VARIABLE POSITION BONE DRILLING ALIGNMENT GUIDE

[75] Inventors: Jon C. Serbousek, Winona Lake; Frank S. Bono, Leesburg, both of Ind.

[73] Assignee: DePuy Orthopaedics, Inc., Warsaw, Ind.

[21] Appl. No.: 09/177,464

[22] Filed: Oct. 22, 1998

[51] Int. Cl.[7] .................................................. A61B 17/17
[52] U.S. Cl. .................. 606/96; 606/70; 606/61
[58] Field of Search ................................ 606/61, 79, 80, 606/96, 98, 104

[56] References Cited

U.S. PATENT DOCUMENTS

| | | | |
|---|---|---|---|
| 4,788,970 | 12/1988 | Kara et al. ................................. | 128/92 |
| 5,112,337 | 5/1992 | Pauos ........................................ | 606/96 |
| 5,152,303 | 10/1992 | Allen . | |
| 5,364,399 | 11/1994 | Lowery et al. . | |
| 5,423,826 | 6/1995 | Coates et al. . | |
| 5,474,555 | 12/1995 | Puno et al. . | |
| 5,634,927 | 6/1997 | Houston et al. . | |
| 5,669,915 | 9/1997 | Caspar et al. ............................. | 606/96 |
| 5,702,447 | 12/1997 | Walch et al. .............................. | 623/16 |
| 5,755,721 | 5/1998 | Hearn . | |

OTHER PUBLICATIONS

"CDH: Preliminary Report on a New Anterior Spinal Instrumentation" by C. Hopf, P. Eysel, and J. Dubousset, published in the European Spine Journal (1995), pp. 194–199.

"Alpha Plaques Cervicales" brochure, published by Stryker.RTM Implants, France, Prior May 1996 (2 pages).

"Cervical Spine Locking Plate, Original Instruments and Implants of the Assoication for the Study of Internal Fixation AO/ASIF" brochure, published by Synthes, Art. No. 036,063, copyright by STRATEC Medical, printed in Switzerland, May 1996.

"Kaneda Anterior Spinal Instrumentation System", p. B–9 from AcroMed Corporation catalog.

"University$^{AM}$ Plate Titanium Anterior System™ Ordering Information for Implants and Instruments" brochure, copyright 1994 AcroMed Corporation (6 pages).

*Primary Examiner*—Michael Buiz
*Assistant Examiner*—Daphna Shai

[57] ABSTRACT

A variable position bone drilling guide apparatus for aiding a surgeon in preparing a bone site. The guide apparatus includes a template that is formed to include apertures therethrough and drill towers extending form the template in general alignment with the apertures. The first drill tower includes at least one drill passage therethrough and the second drill tower includes two drill passages therethrough. The duel passages in the second tower provide a surgeon with greater than one drill alignment option for a bone plate.

15 Claims, 7 Drawing Sheets

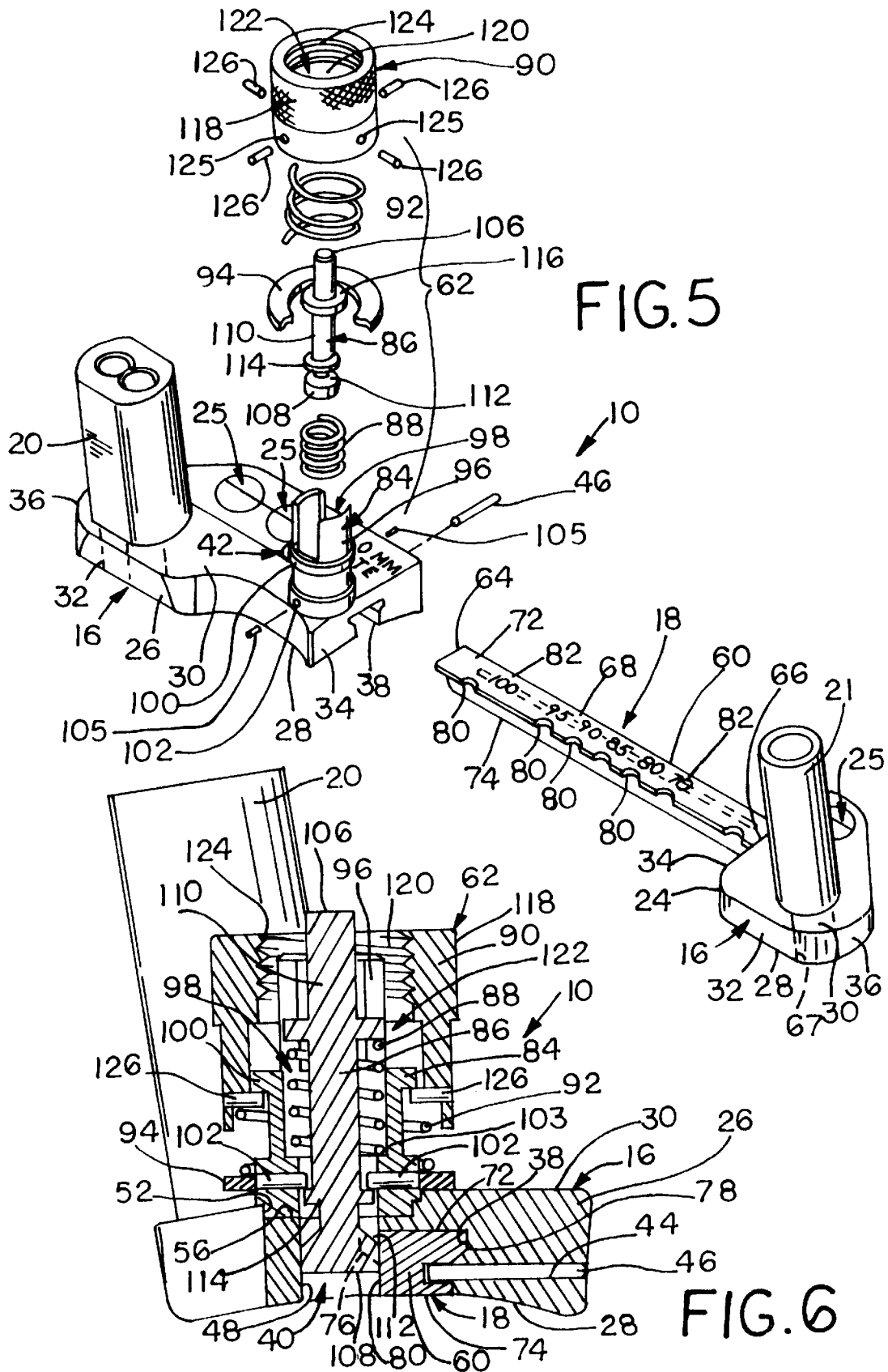

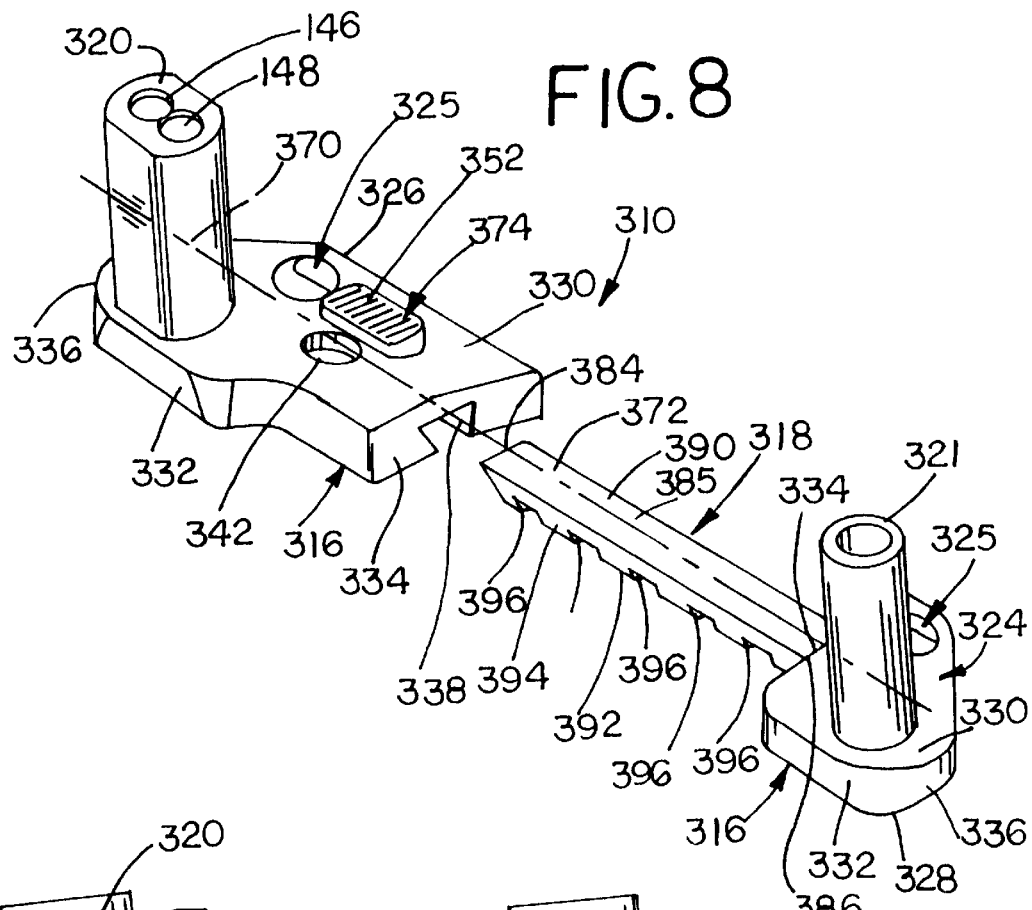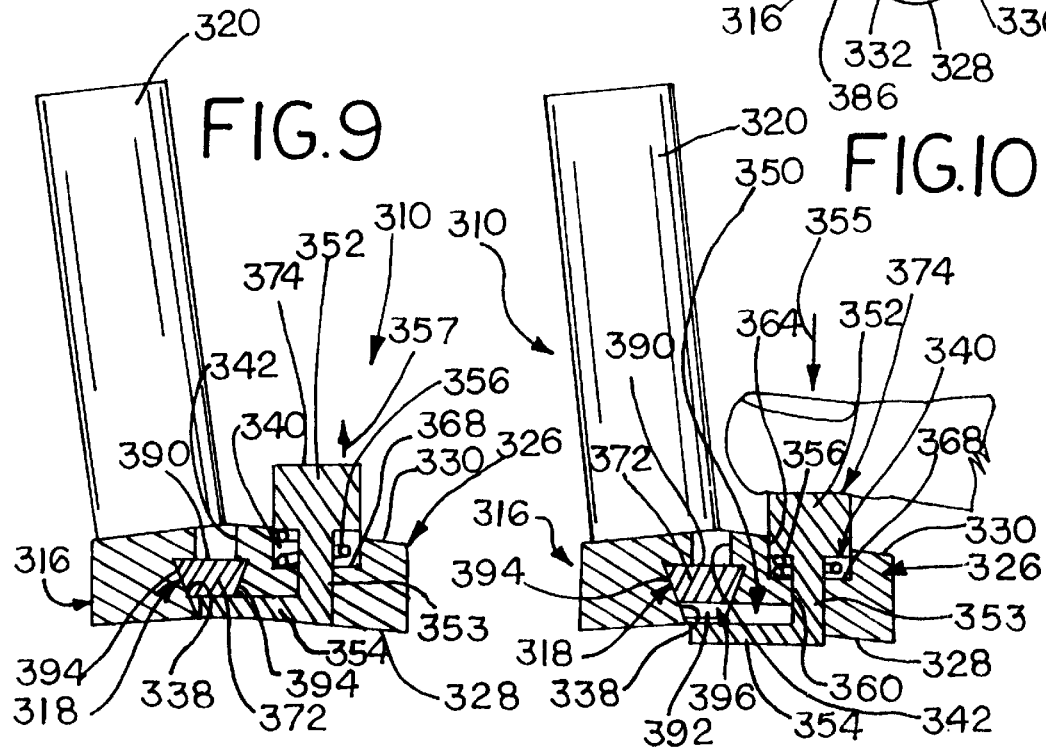

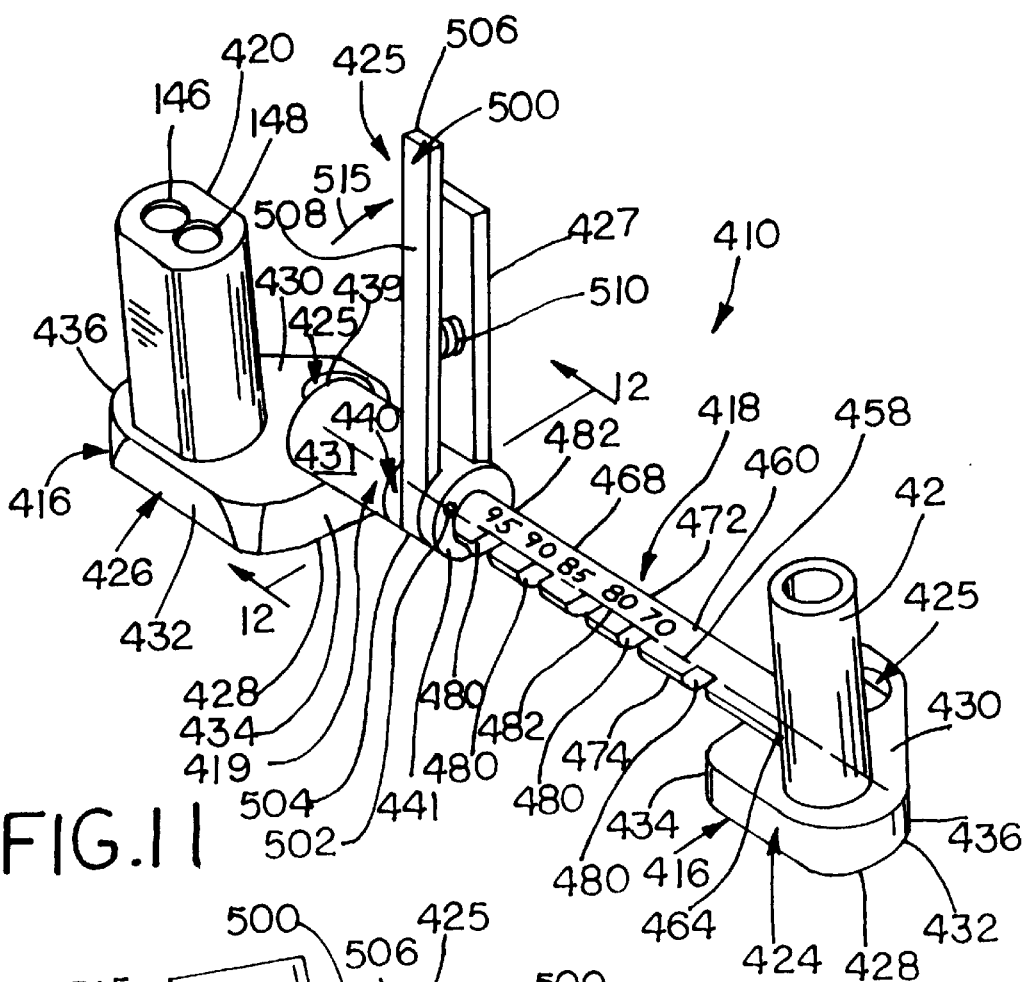
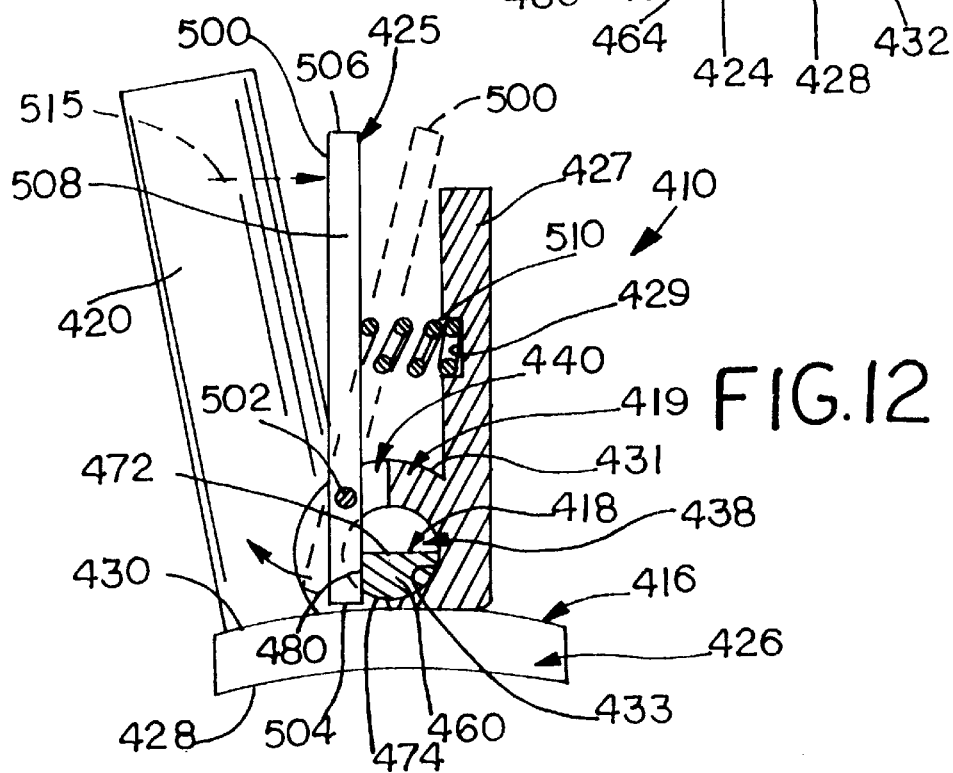

VARIABLE POSITION BONE DRILLING ALIGNMENT GUIDE

BACKGROUND AND SUMMARY OF THE INVENTION

A surgical instrument is provided in accordance with the present invention to aid a surgeon in preparing a bone site. Specifically, the surgical instrument is formed to aid a surgeon in sizing and preparing a pre-determined bone site for one of numerous length plates.

Drill guides for orthopaedic use are known. See for example U.S. Pat. No. 5,634,927 to Houston et al.; U.S. Pat. No. 5,364,399 to Lowery et al; and U.S. Pat. No. 5,755,721 to Hearn. These references are incorporated herein for teaching the general purposes and situations of drill guides.

According to the present invention, a variable position bone drilling guide apparatus is provided. The guide apparatus includes a template that is formed to include apertures therethrough and drill towers extending from the template in general alignment with the apertures. The first drill tower includes at least one drill passage therethrough and the second drill tower includes two drill passages therethrough. The duel passages in the second tower provide a surgeon with greater than one drill alignment option for a bone plate.

In preferred embodiments, the template of the guide apparatus includes separate locking and sliding bodies and the one of the drill towers is coupled to each body. In addition, a telescopic mechanism extends between the sliding and locking bodies to permit movement of template between an expanded position and a retracted position. Thus, guide apparatus telescopes in order to size and prepare a bone site for one of numerous length bone plates within a family of plates. The telescopic mechanism includes a lock bar that is coupled to the locking body and formed for sliding movement relative to the sliding body. In addition, a button is coupled to the sliding body to couple the lock bar and prevent movement of the lock bar relative to the sliding body.

Additional features of the invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 5 is an exploded perspective view of the apparatus of FIG. 1, showing the button including a button tower coupled to the locking body and defining a passageway, a first spring sized for extension into the passageway, the shaft formed for extension through the spring and into the passageway, a seat sized for extension about the button tower, a second spring, and the sleeve formed for extension over the shaft and the button tower, FIG. 6 is a view similar to FIG. 4 following removal of the handle from the button showing the shaft biased through the passageway into engagement with the lock slot of the lock bar to couple the lock bar in fixed position relative to the locking body;

FIG. 8 is a perspective view of an alignment guide apparatus of the present invention including a template, a telescopic mechanism, and drill and tap towers, showing the template including a locking body and a sliding body, the sliding body including a channel that receives the telescopic mechanism and the telescopic mechanism including a lock bar that extends through the channel and has lock notches therein and a push-button clamp that engages the notches of the lock bar to hold the lock bar in a fixed position relative to the bodies;

FIG. 9 is a cross-sectional view of the alignment guide apparatus of FIG. 8, showing the push-button clamp including a push button, first arm extending from the push button, and a second arm extending from the first arm and engaging the lock bar;

FIG. 10 is a view similar to FIG. 9, showing the push button manually depressed and the second arm disengaging the bar to allow the bar to slide in the channel and move the towers relative to one another;

FIG. 11 is a perspective view of an alignment guide apparatus of the present invention including a template having locking and sliding bodies, a telescopic mechanism, and drill and tap towers, showing the telescopic mechanism having a mount coupled to the sliding body, a lock bar extending through the mount, and a lock clip coupled to the mount; and FIG. 12 is a view taken along lines 12—12 of FIG. 11 showing the lock clip extending into a lock slot of the lock bar, the lock clip including a arm pivotably coupled to the mount, the first arm extending into one of the lock slots to block the sliding movement of the bar through the mount.

DETAILED DESCRIPTION OF THE DRAWINGS

Figure 1:
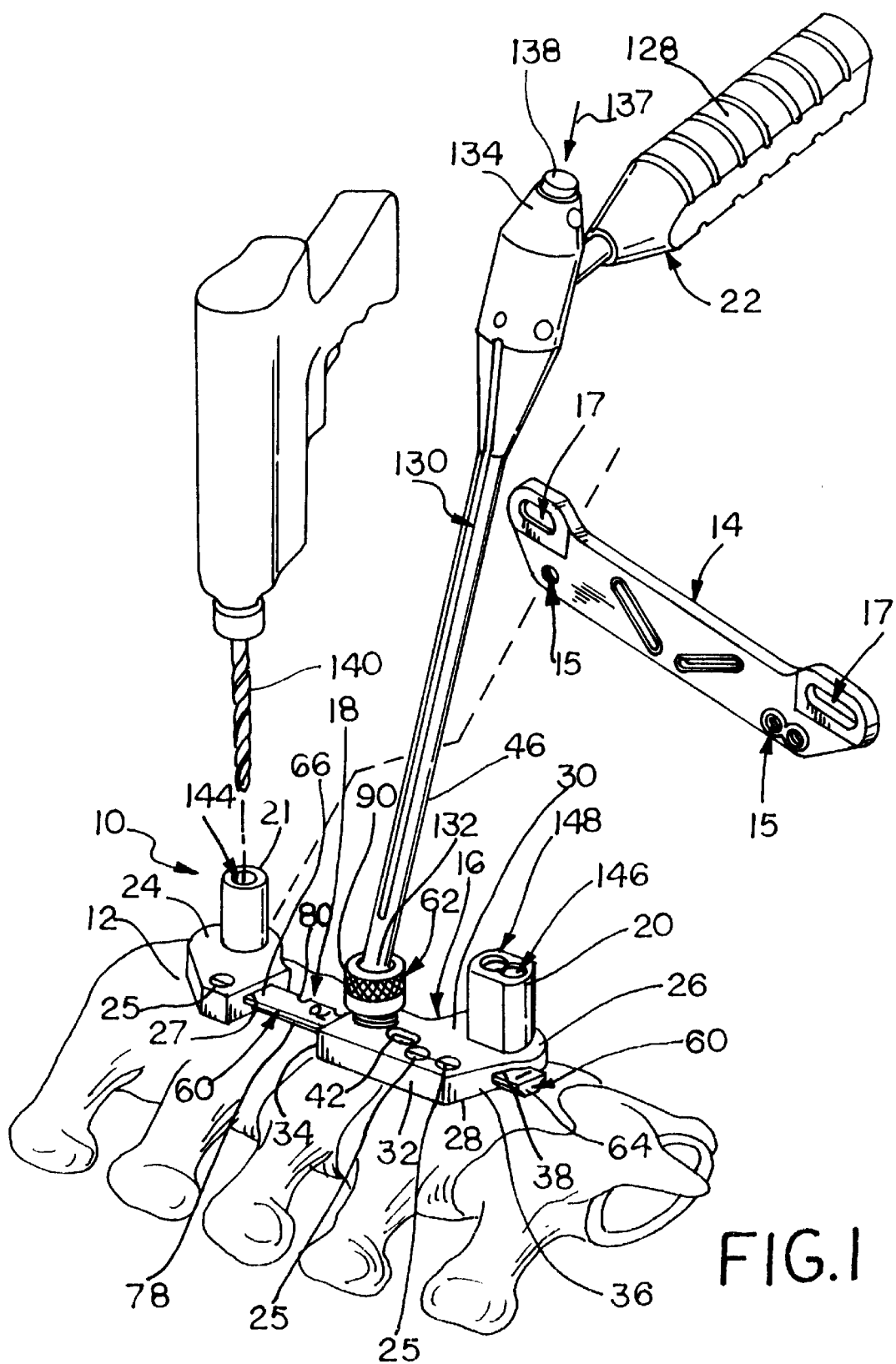
FIG. 1 is a perspective view of an alignment guide in accordance with the present invention as it would appear to a surgeon during use, showing the alignment guide including a template resting on a vertebrae, a telescopic mechanism coupled to the template, and drill and tap towers, a drill in general alignment with one of the drill towers, and a handle coupled to the telescopic mechanism, and a bone plate spaced-apart from the template.

As shown in FIG. 1, a bone drilling guide apparatus 10 is provided in accordance with the present invention. Guide apparatus 10 telescopes in order to size and prepare a pre-determined bone site 12 for one of numerous length plates 14. Thus, the surgeon may enter a wound site a single time, but be provided with a multitude of drill/alignment options. Apparatus 10 includes a template 16, a telescopic mechanism 18, and drill and tap towers 20, 21. A handle 22, as shown in FIG. 1 is also provided for gripping template 16 during the surgical procedure. While plate 14 is illustrated and described, it is understood that apparatus 10 may be used with any number of bone plates.

Template 16 includes a locking body 24 and a sliding body 26. Locking and sliding bodies 24, 26 each include an inferior surface 28 and a superior surface 30. See FIG. 1. Inferior surface 28 is generally shaped to mate with bone site 12. A perimeter edge 32 extends between inferior and superior surfaces 28, 30 and includes a medial portion 34 and a lateral portion 36. Medial portions 34 of locking and sliding bodies 24, 26 are positioned to face one another. In addition, tap towers 20, 21 extend away from superior surface 30 adjacent to lateral portion 36 of locking and sliding bodies 24, 26 respectively. Locking body 24 and sliding body 26 are formed to include generally semi-circular shaped apertures 25 to enable the surgeon to visualize bone site 12. In addition, locking body 24 includes a slot 27 that receives telescopic mechanism 18.

Figure 4:
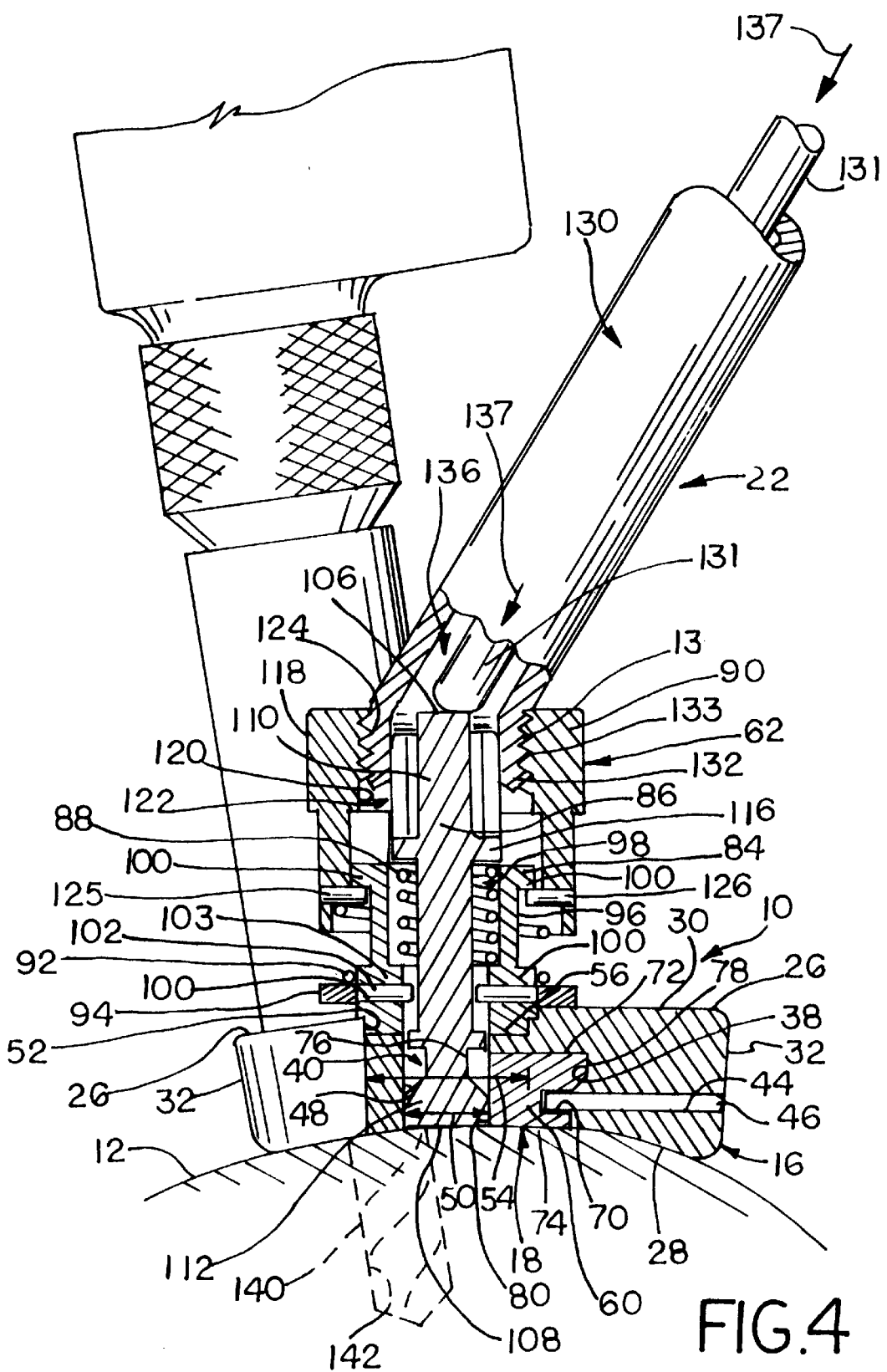
FIG. 4 is a cross-sectional view of apparatus following the coupling of the handle to the button and the extension of the drill bit through the drill tower, showing the button including a threaded sleeve and a shaft extending through the sleeve into the channel and the handle including a handle driver shaft including a threaded end coupled to the sleeve and a movable rod extending into the button to move the shaft away from the lock slot to permit movement of the lock bar in the channel.

Referring now to FIG. 1, inferior surface 28 of sliding body 26 is formed to include a channel 38 that receives telescopic mechanism 18. Channel 38 extends between medial portion 24 and lateral portion 26. As shown in FIG. 4, an aperture 40 extends between superior and inferior surfaces 30, 28 and intersects channel 38. Aperture 40 is defined by an inferior inner wall 48 adjacent to inferior surface 28 and has a first dimension 50 and a superior inner wall 52 adjacent to superior surface 30 and has a second dimension 54 that is greater than first dimension 50. Walls 48, 52 cooperate to define seat 56. Sliding body 26 also includes a window 42 that extends through superior surface 30 in general alignment with channel 38. A passageway 44 extends between edge 32 and channel 38 to receive a guide pin 46 therein.

Figure 2:
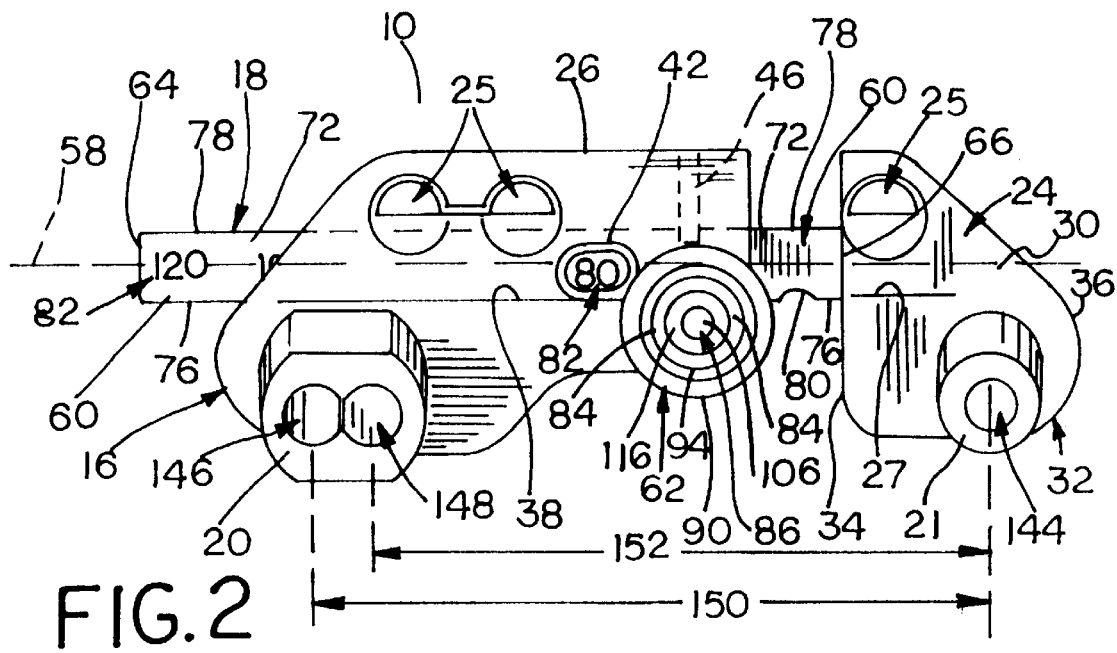
FIG. 2 is a top view of the alignment guide of FIG. 1 showing the template including a locking body, a sliding body coupled to the locking body by the telescopic mechanism and the sliding body including a channel formed therein to receive the telescopic mechanism and a window in general alignment with the channel to view indicia positioned on the telescopic mechanism.
Figure 3:
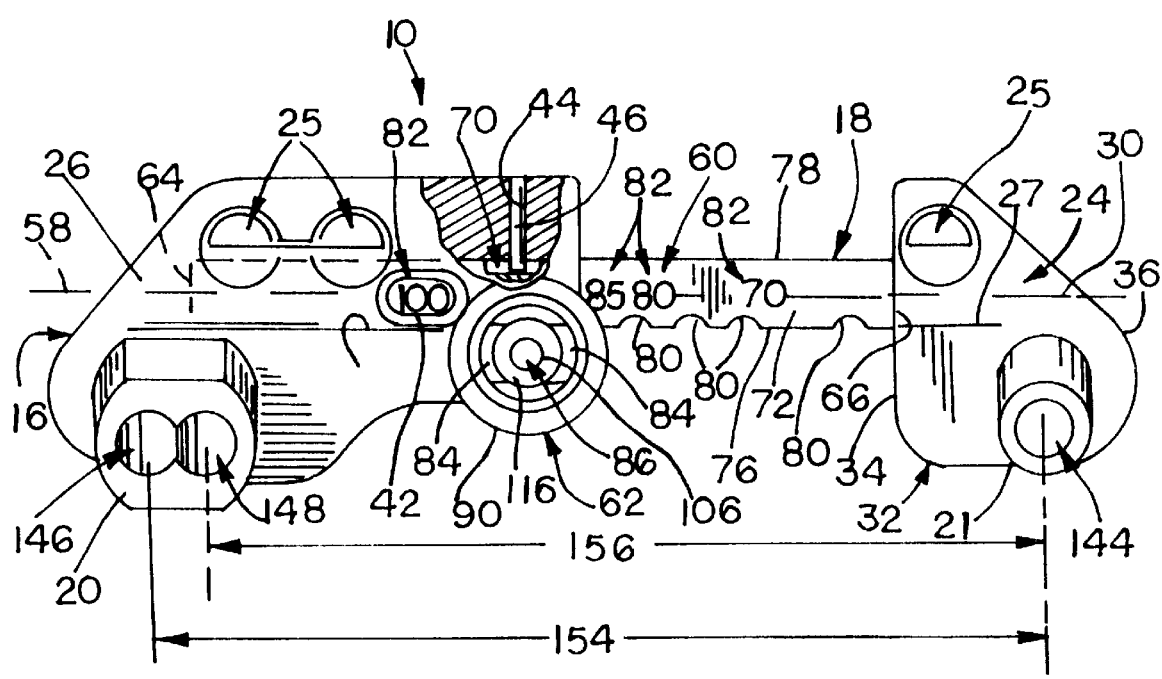
FIG. 3 is a view similar to FIG. 2 of the alignment guide following movement of the sliding body away from the locking body, showing the telescopic mechanism including a lock bar that extends through the channel and a button that engages the lock bar to hold the lock bar in a fixed position relative to the bodies.

Referring now to FIG. 2, telescopic mechanism 18 is coupled in slot 27 of locking body 24. Telescopic mechanism 18 provides the surgeon with intuitive lock/unlock action and prevents rotational movement of bodies 24, 26 about an axis 58 that extends between bodies 24, 26. Telescopic mechanism 18 includes a lock bar 60 extending through channel 38 and a button 62 coupled to locking body 24. As shown in FIGS. 2 and 3, the relative movement of bodies 24, 26 along axis 58 is limited by a pre-determined length of lock bar 60. Lock bar 60 extends through channel 38 of sliding body 26 and includes opposite ends 64, 66 and a middle portion 68 extending between opposite ends 64, 66. First end 64 of lock bar 60 is movable relative to sliding body 26 while second end 66 of lock bar 60 is coupled in slot 27 of locking body 24. As shown in FIGS. 3 and 4, a slot 70 having a predetermined length is formed in middle portion 68 of lock bar 60. Slot 70 is sized to permit sliding movement of guide pin 46 therein, but engages guide pin 46 when sliding body 26 is spaced apart from locking body a predetermined expanded distance. Thus, guide pin 46 cooperates with lock bar 60 to limit the distance sliding body 26 is permitted to travel along axis 58 away from locking body 24.

As shown in FIG. 4, middle portion 68 of lock bar 60 includes a superior side 72, an inferior side 74, a dovetail edge 76 extending between superior and inferior sides 72, 74, and a guide edge 78. Additionally, middle portion 68 includes lock slots 80 in dovetail edge 76. The shape of lock bar 60 may be generally round, oval, triangular, or any number of shapes in accordance with this disclosure so long as first end 64 is movable relative to locking body 26 and middle portion 68 slides through channel 38. Lock slots 80 are generally spaced-apart relative to one another a pre-determined distance that correspond with pre-determined lengths of various bone plates 14

Indicia 82 are formed on superior side 72 of lock bar 60 that correspond with each lock slot 80. Indicia 82 are aligned with window 42 to provide the surgeon with a visual cue that corresponds with the selected length of plate 14. Lock bar 60 preferably includes lock slots 80 that correspond with plate lengths ranging from about 50 mm to about 120 mm. For example, plate lengths may include 50 mm, 60 mm, 70 mm, 80 mm, 85 mm, 90 mm, 95 mm, 100 mm, 110 mm, and 120 mm. It is understood, however, that middle portion 68 may be formed with various numbers of lock slots 80 and lock slots 80 may be associated with a wide variety of plate lengths less than about 50 mm and greater than about 120 mm in accordance with the present disclosure.

Button 62 of telescopic mechanism 18 cooperates with lock slots 80 to hold bodies 24, 26 in a fixed position relative to one another along axis 58. As best shown in FIGS. 5 and 6, button 62 includes a button tower 84 coupled to sliding body 26, a shaft 86 extending through button tower 84, a first spring 88 extending about shaft 86, a sleeve 90 extending over button tower 84, and a second spring 92 extending between button tower 84 and seat 94. As shown in FIG. 5, button tower 84 includes a side wall 96 defining a passageway 98 and a tab 100 extending from side wall 96. In addition, side wall 96 includes opposing apertures 102 in communication with passageway 98. Each aperture 102 is sized to receive a pin 105 to couple button tower 84 to sliding body 26. In addition, a spring seat 103 extends into passageway 98 adjacent to apertures 102.

Shaft 86 extends through passageway 98 of button tower 84 and into aperture 40 of sliding body 26. Shaft 86 includes opposite ends 106, 108 and a center portion 110 extending between opposite ends 106, 108. As shown in FIG. 5, one end 108 of shaft 86 includes a dove-tail portion 112 positioned in aperture 40. In addition, a tab 114 extends from center portion 110 adjacent to end 108 to engage lock bar 60 and prevent shaft 86 from sliding through aperture 40 away from inferior surface 28 of sliding body 26. A spring mount 116 also extends from center portion 110 spaced-apart from tab 114. Spring 88 extends between spring seat 103 of button tower 84 and spring mount 116 to normally bias dove-tail portion 112 away from inferior surface 28 of sliding body 26 and into engagement with lock slots 80 of lock bar 60.

Sleeve 90 extends over button tower 84 and includes an exterior surface 118 and an interior surface 120 that defines a passageway 122. Interior surface includes threads 124. In addition, as shown in FIG. 5, sleeve 90 includes apertures 125 to receive pin 126. Pin 126 couples sleeve 90 to button tower 84. In addition, spring 92 extends between pin 126 and seat 94 to normally bias sleeve 90 away from sliding, plate 26 to position end 106 of shaft 86 within passageway 122. While pins 126 are illustrated and described, it is understood that sleeve 90 may be coupled to button tower 84 in a variety of manners in accordance with the present disclosure.

Referring again to FIG. 1, drill and tap towers 20, 21 of apparatus 10 are coupled to locking, and sliding bodies 24, 26 of template 18 for sighting, drilling, and tapping for the two most extreme bolt locations and the middle location of the long compression slot of plate 14. Towers 20, 21 are aligned with apertures 69 and 71, and 67 formed in locking and sliding bodies 26, 24 respectively. Referring now to FIG. 2, tower 21 in locking body 24 includes a single drill passage 144. Tower 20 in sliding body 26, however, includes duel drill passages 146, 148. Passages 146, 148 are spaced-apart such that when template 18 is positioned in a retracted position, as shown in FIG. 2, passages 144, 146 are spaced-apart a first distance 150 and passages 144, 148 are spaced-apart a second distance 152 that is less than first distance 150. Likewise, when template 18 is in an expanded position as shown in FIG. 3, passages 144, 146 are spaced-apart a third distance 154 and passages 144, 148 are spaced-apart a fourth distance 156 that is less than third distance 154. While towers 20, 21 are illustrated and described, towers may be positioned in a variety of locations on locking and sliding bodies and may be formed in a variety of shapes and sizes in accordance with this disclosure. It is appreciated that while button is illustrated and described, that a numerous mechanisms such as a wing nut/screws, clamps, fasteners, hooks, and the like may be used to couple lock bar 60 and hold locking and sliding bodies 24, 26 in a fixed position relative to one another.

Handle 22 is shown in FIGS. 1 and 4. Handle 22 is formed to couple button 62 to enable surgeon to move template 18 from one location to another. Handle 22 includes a hand grip 128 coupled to a driver shaft 130 and a rod 131 extending through driver shaft 130. Driver shaft 130 extends away from sliding body 26 of template 18 generally normal to curvature and has a length of about five to six inches. Driver shaft 130 may, however, be coupled to locking body 124 and vary in length. Driver shaft 130 includes a first end 132 having threads 133 formed to couple with threads 124 of sleeve 90, an opposite second end 134, and a passageway 136 extending between first and second ends 132, 134. See FIG. 4.

As shown in FIG. 4, rod 131 extends through passageway 136 between first and second ends 132, 134. Referring now to FIG. 1, rod 131 is coupled to a push-button 138 that extends from passageway 136 adjacent to second end 134. Rod 131 is sized to engage end 106 of shaft 86 and extend into passageway 122 to disengage dove-tail portion end 108 from lock slot 80 and permit movement of lock bar 60 in channel 38.

In operation, the surgeon rotates end 132 of driver shaft 130 in passageway 122 of sleeve 90 until threads 124, 133 are coupled together. Once driver shaft 130 is coupled to button 62, locking body 24 of template 18 is aligned with a pre-determined bone site 12. Drill and tap tower 21 may be used for sighting a desirable bone site. After bone site 12 has been selected, a drill bit 140 is inserted through drill and tap tower 21 on locking body 24 and a hole (not shown) is formed in bone. After the hole has been drilled, a tap (not shown) may be inserted through drill and tap tower 21 to enlarge the diameter of the hole to receive a bolt (not shown) therethrough. Bolt (not shown) is formed for extension through slots 17 in bone plate 14.

If tower 20 on sliding body 26 is not in alignment with a desirable bone site 12, the surgeon can move sliding body 26 away from or toward locking body 24. To move sliding body 26, the surgeon must simply press push-button 138, as shown by arrow 137, and move hand grip 128 in the desired direction. When push-button 138 is depressed, rod 131 moves along arrow 137 and presses shaft 86 against spring 88 toward inferior surface 28 of sliding body 26. At this time, dove-tail portion 112 disengages lock slot 80 of lock bar 60, as shown in FIG. 4, to permit lock bar 60 to slide freely in channel 38 toward a desired direction. As lock bar 60 slides in channel 38, indicia 82, which reflect a corresponding size of plate 14, are visible to the surgeon through window 42, as shown in FIGS. 2 and 3. Once a desirable bone site 12 is selected, the surgeon must simply release push-button 138. At this time, as shown in FIG. 6, spring 88 presses dove-tail portion 112 toward lock bar 60. If dove-tail portion 112 is in alignment with lock slot 80, lock bar 60 will be fixed in position, as shown in FIG. 6. If, however, dove-tail portion 112 is spaced-apart from lock slot 80, lock bar 60 will be free to slide in channel 38 to an adjacent lock slot 80. Surgeon may then select passage 146, 148 of tower 20 to guide drill bit 140 to form hole 142 in selected bone site 12 and to guide tap (not shown) following removal of drill bit 140.

Figure 7:
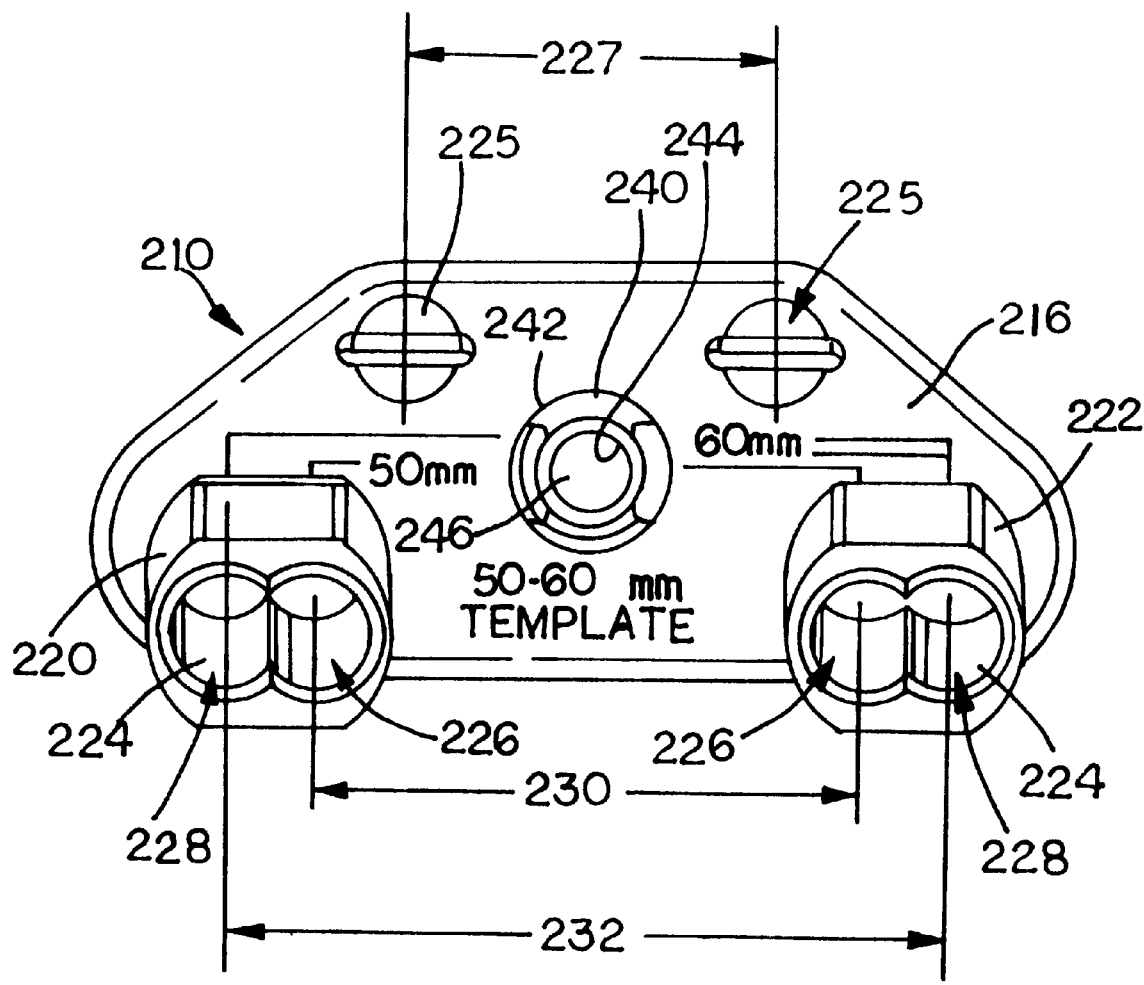
FIG. 7 is a top view of an alignment guide apparatus of the present invention including a template and drill and tap towers extending from the template the towers each including due passages.

Referring now to FIG. 7, an alignment guide apparatus 210 in accordance with the present invention is provided. Apparatus 210 is formed to prepare a pre-determined bone site 12 for different lengths of bone plates 14. Thus, the surgeon may enter a wound site a single time, but be provided with a greater than one drill/alignment option. Apparatus 210 includes a template 216, drill and tap towers 220, 222, and a grip portion 240. Template 216 includes generally semi-circular shaped apertures 225 spaced apart a pre-determined distance 227. Distance 227 corresponds to a distance between screw holes 15 in bone plate 14. Apertures 225 enable the surgeon to visualize bone site 12. Grip portion 240 includes a shell 242 that includes a threaded interior 244 that defines a passageway 246. Shell 242 is formed in a manner similar to sleeve 90 as previously discussed and therefore, handle 22, as shown in FIG. 1 may be used to couple grip portion 240 during the surgical procedure. It is understood, however, that a handle suitable for use with grip portion 240 need not include rod 131.

Drill and tap towers 220, 222 of apparatus 210 are coupled to template 218 for sighting, drilling, and tapping for the two most extreme bolt locations and the middle location of the long compression slot of plate 214. As shown in FIG. 7, towers 220, 222 each include an inner surface 224 that defines duel drill passages 226, 228.

Passages 226 are spaced-apart from one another a distance 230, which is about 50 mm. Passages 228 are spaced-apart from one another a distance 232, which is about 60 mm.

In use, a surgeon coupled handle 22 to grip portion 240 in a manner similar to that described above with reference to handle 22 and sleeve 90. Once handle 22 is coupled to grip portion 240, template 218 is aligned with a pre-determined bone site 12. Drill and tap towers 220, 222 may be used for sighting a desirable bone site. The surgeon may then select the desirable passageways 224, 226 that correspond with an appropriate sized bone plate.

A bone drilling guide apparatus 310 is also provided in accordance with the present invention and shown in FIGS. 8–10. Guide apparatus 310 telescopes in order to size and prepare a pre-determined bone site 12 for one of numerous length plates 14. Thus, the surgeon may enter a wound site a single time, but be provided with a multitude of drill/alignment options. Apparatus 310 includes a template 316, a telescopic mechanism 318, and drill and tap towers 320, 321. Towers 320, 321 are formed in a similar manner to towers 20, 21 as previously described and like reference numerals will be used to denote like components.

Template 316 includes a locking body 324 and a sliding body 326. Locking and sliding bodies 324, 326 each include an inferior surface 328, a superior surface 330, and semi-circular shaped apertures 325 therethrough. Apertures enable the surgeon to visualize bone site 12. See FIGS. 9 and 10. Inferior surface 328 is generally shaped to mate with bone site 12. A perimeter edge 332 extends between inferior and superior surfaces 328, 330 and includes a medial portion 334 and a lateral portion 336. Medial portions 334 of locking and sliding bodies 324, 326 are positioned to face one another. In addition, Tap towers 320, 321 extend away from superior surface 330 adjacent to lateral portion 336 of locking and sliding bodies 324, 326 respectively. Locking body 324 is formed to include a slot (not shown) that receives telescopic mechanism 318.

Referring now to FIG. 9, inferior surface 328 of sliding body 326 is formed to include a channel 338 that receives telescopic mechanism 318. Channel 338 extends between medial portion 324 and lateral portion 326. An aperture 340 extends between superior and inferior surfaces 330, 328 adjacent to channel 338. Aperture 340 is defined by an inferior portion 360, a superior portion 364, and a seat 368 positioned to lie between inferior and superior portions 360, 364. As best shown in FIG. 10, a secondary channel 350 is formed in inferior surface 328 and extends between inferior portion 360 of aperture 340 and channel 338. Sliding body 324 also includes a window 342 extending through superior surface 330 in general alignment with channel 338.

Referring now to FIG. 8, telescopic mechanism 318 provides the surgeon with intuitive lock/unlock action and rotational control relative to an axis 370 extending between locking and sliding bodies 324, 326. Telescopic mechanism 318 includes a lock bar 372 that extends through channel 338 of sliding body 326 and is coupled to medial edge 334 of locking body 326. Telescopic mechanism 318 also includes a push-button clamp 374 that extends through aperture 340 and engages lock bar 372 to hold lock bar 372 in a fixed position relative to locking and sliding bodies 324, 326.

The relative movement of bodies 324, 326 along axis 370 is limited by a pre-determined length of lock bar 372. Lock bar 372 extends through channel 338 of sliding body 326 and includes opposite ends 384, 386 and a middle portion 388 extending between opposite ends 384, 386. First end 384 of lock bar 372 is movable relative to sliding body 326 while second end 386 of lock bar 372 is coupled to medial portion 334 of locking body 324. As shown in FIG. 9, middle portion 388 of lock bar 372 includes a superior side 390, an inferior side 392, and dovetail edges 294 extending between superior and inferior sides 390, 392. Additionally, inferior side 392 includes lock slots 396. Lock slots 396 are generally spaced-apart relative to one another a pre-determined distance that correspond with pre-determined lengths of bone plates 14. Indicia (not shown) are formed on superior side 390 that correspond to each lock slot 396. Indicia are aligned with window 342 to provide the surgeon with a visual cue that corresponds with the selected plate length as previously discussed with apparatus 10.

Push-button clamp 374 is shown in FIGS. 9 and 10. Push-button clamp 374 is generally L-shaped and includes a push-button 352 extending into aperture 340 adjacent to superior portion 364, a first arm 353 extending from push-button 352 toward inferior surface 328, a second arm 354 extending from first arm 353 through secondary channel 350, and a spring 356 extending between push-button 352 and seat 368. As shown in FIGS. 9 and 10, second arm 354 is sized for extension into lock slots 396 to couple locking and sliding bodies 324, 326 in a fixed position along axis 370 relative to one another. Spring 356 normally biases push-button 352 toward a locking position as shown in FIG. 9, where second arm 354 extends into lock slot 396 and sliding movement of lock bar 372 in channel 338 is blocked.

In operation, a bone site 12 is selected and a drill bit similar to bit 140 of FIG. 1 is inserted through drill and tap tower 321 on locking body 324 and a hole (not shown) is formed in the bone. After the hole has been drilled, a tap (not shown) may be inserted through drill and tap tower 321 to enlarge the diameter of the hole, as previously discussed with reference to apparatus 10. If tower 320 on sliding body 326 is not in alignment with a desirable bone site 12, the surgeon can move sliding body 326 away from or toward locking body 324. To move sliding body 326, the surgeon must simply manually depress press push-button 352 as shown by arrow 355 in FIG. 10 and move tower 320 in the desired direction. When push-button 352 is depressed, first arm 353 moves in direction 355 against spring 356 toward inferior surface 328 of sliding body 326. At this time, second arm 354 disengages lock slot 396 of lock bar 372, as shown in FIG. 10 permitting lock bar 372 to slide freely in channel 338 in a desired direction. As lock bar 328 slides in channel 338, indicia (not shown), which reflect a corresponding size of plate 14, are visible to the surgeon through window 342.

Once a desirable bone site 12 is selected, the surgeon must simply release push-button 352. At this time, as shown in FIG. 9, spring 356 presses push-button 352 away from seat 368 as shown by arrow 357 and second arm 354 into lock slot 396. If second arm 354 is in alignment with lock slot 396, lock bar 372 will be fixed in position, as shown in FIG. 9. If, however, second arm 354 is spaced-apart from lock slot 396, lock bar 372 will be free to slide in channel 338 to an adjacent lock slot 396. Surgeon may then select passage 146, 148 of tower 320 to guide drill bit 140 to form a hole in selected bone site 12 and to guide tap (not shown) following removal of the drill bit, as previously discussed with reference to apparatus 10.

As shown in FIGS. 11 and 12, a bone drilling guide apparatus 410 is provided in accordance with the present invention. Guide apparatus 410 telescopes in order to size and prepare a pre-determined bone site 12 for one of numerous length plates 14. Thus, the surgeon may enter a wound site a single time, but be provided with a multitude of drill/alignment options. Apparatus 410 includes a template 416, a telescopic mechanism 418, and drill and tap towers 420, 421. Towers 420, 421 are formed in a manner similar to towers 20, 21 and like reference numerals will be used to denote like components.

Template 416 includes a locking body 424 and a sliding body 426. Locking and sliding bodies 424, 426 each include an inferior surface 428, a superior surface 430, and generally semi-circular apertures 425 extending between surfaces 428, 430. See FIG. 1. Apertures 425 enable the surgeon to visualize bone site 12. Inferior surface 428 is generally shaped to mate with bone site 12. A perimeter edge 432 extends between inferior and superior surfaces 428, 430 and includes a medial portion 434 and a lateral portion 436. Medial portions 434 of locking and sliding bodies 424, 426 are positioned to face one another. In addition, Tap towers 420, 421 extend away from superior surface 430 adjacent to lateral portion 436 of locking and sliding bodies 424, 426 respectively.

Referring now to FIG. 12, telescopic mechanism 18 is coupled between bodies 424, 426. Telescopic mechanism 418 provides the surgeon with intuitive lock/unlock action and prevents rotational movement of bodies 424, 426 about an axis 458 that extends between bodies 424, 426. Telescopic mechanism 418 includes a mount 419 coupled to superior surface 430 of sliding body 426, a lock bar 460 coupled to locking body 424 and extending through mount 419, and a lock clip 425 coupled to mount 419.

Mount 419, as shown in FIG. 11, includes an exterior surface 431 and an interior surface 433 that defines a channel 438 that receives lock bar 460. Mount 419 further includes a first end 439 adjacent to medial portion 434 and a second end 441 spaced-apart from sliding body 426. Channel 438 extends between first and second ends 439, 441. As shown in FIG. 11, a notch 440 extends between through exterior surface 431 for receiving lock clip 425. Referring now to FIG. 12, mount 419 further includes a handle 427 that extends from exterior surface 431 away from superior surface 430 of locking body 426. Handle 427 includes a spring mount 429 formed therein.

Lock bar 460 extends through channel 438 of sliding body 426 and includes opposite ends 464 and a middle portion 468 extending between opposite ends 464. End 464 adjacent to mount 419 includes a stop tab (not shown) sized to engage end 439 of mount 419 to limit the distance sliding body is permitted to travel along axis away from locking body. As shown in FIG. 11, middle portion 468 of lock bar 460 includes a superior side 472 and a generally curved inferior side 474 formed to include lock slots 480. Lock slots 480 are generally spaced-apart relative to one another a pre-determined distance that correspond with pre-determined lengths of bone plate 14. Indicia 482 are formed on superior side 472 of lock bar 460 that correspond to each lock slot 480. Indicia 482 are aligned with end 441 of mount 419 to provide the surgeon with a visual cue that corresponds with the selected plate length.

Lock clip 425 is shown in FIG. 11. Lock clip 425 extends through notch 440 formed in mount 419 and extends into one locking slot 480 to couple locking and sliding bodies 424, 426 in a fixed position along axis 458 relative to one another. Lock clip 425 includes an arm 500 having a first end 504 coupled to mount 419, an opposite free end 506, and a middle portion 508 that extends between ends 504, 506 spaced-apart from handle 427. A pin 502 extends through first end 504 to pivotably couple arm 500 to mount 419 in notch 440. A spring 510 extends between mount 429 and middle portion 508 to bias arm 500 to a locking position shown in FIGS. 11 and 12, where arm 500 extends into lock slot 480.

In operation, a bone site 12 is selected and a drill bit 140 is inserted through drill and tap tower 421 on locking body 424 and a hole is formed in the bone. After the hole has been drilled, a tap (not shown) may be inserted through drill and tap tower 21 to enlarge the diameter of the hole, as previously discussed with reference to apparatus 10. If tower 420 on sliding body 426 is not in alignment with a desirable bone site 12, the surgeon can move sliding body 426 away from or toward locking body 424. To move sliding body 426, the surgeon manually presses arm 500 toward handle 427 as shown by arrow 515 in FIG. 11 and moves tower 420 in the desired direction. When arm 500 is moved, as shown in phantom in FIG. 12, end 504 of arm pivots away from lock slot 460, to permit lock bar 460 to slide freely in channel 438 in a desired direction. As lock bar 460 slides in channel 438, indicia 468, which reflect a corresponding size of plate 14, are visible to the surgeon adjacent to end 441 of mount 419.

Once a desirable bone site 12 is selected, the surgeon must simply release arm 500. At this time, spring 510 urges end 504 into lock slot 480. If arm 500 is in alignment with lock slot 480, lock bar 460 will be fixed in position, as shown in FIG. 12. If, however, arm 500 is spaced-apart from lock slot 480, lock bar 460 will be free to slide in channel 438 to an adjacent lock slot 480. The surgeon may then select passage 146, 148 of tower 420 to guide drill bit 140 to form hole 142 in selected bone site 12 and to guide tap (not shown) following removal of drill bit 140, as previously discussed with reference to apparatus 10.

Therefore guide apparatuses of the present invention give the surgeon the ability to enter a wound site one time and have a multitude of drill/alignment options. In addition, apparatus 10, 310, 310 telescopes in order to size and prepare the bone site for one of numerous length plates within a family of plates.

Although the invention has been described with reference to certain embodiments, variations exist within the scope and spirit of the invention as described and defined in the following claims.

What is claimed is:

1. A bone drilling guide apparatus comprising:
    a template including a body having an inferior surface, a superior surface and apertures extending between the inferior and superior surfaces,
    first and second drill towers extending from the superior surface of the template, the first drill tower including at least one drill passage therethrough in alignment with at least one aperture in the template and the second drill tower including two drill passages therethrough and alignment with two apertures formed in the template;
    the template including a locking body and a sliding body spaced apart from the locking body; and
    a telescopic mechanism extending between the locking and sliding bodies to permit movement of the template between an expanded position and an retracted position;
    the telescopic mechanism including a lock bar coupled to the locking body and formed for sliding movement relative to the sliding body, and a lock which engages the lock bar to lock the locking body and sliding body in position relative to one another and disengages the lock bar to permit adjustment of the relative position of the locking body and the sliding body.

2. The apparatus of claim 1, wherein the first drill tower includes two drill passages.

3. The apparatus of claim 2, further comprising a grip portion adapted to couple to a handle.

4. The apparatus of claim 3, wherein the grip portion includes a shell that has a threaded interior.

5. The apparatus of claim 1 wherein the first drill tower is coupled to the locking body and the second drill tower is coupled to the sliding body.

6. A bone drilling guide apparatus comprising:
    a template including a sliding body and a locking body,
    first and second drill towers extending from the sliding and locking bodies respectively, the drill towers including at least one drill passage therethrough, and
    a telescopic mechanism extending between the sliding and locking bodies to permit movement of the template between an expanded position and an retracted position, the telescopic mechanism including a lock for engaging the locking body to lock the locking body and sliding body in position relative to one another, and disengaging the locking body to permit adjustment of the relative position of the locking body and the sliding body.

7. The apparatus of claim 6, wherein the sliding body is formed to include a channel therethrough and the lock bar extends through the channel.

8. The apparatus of claim 6, wherein the lock bar includes indicia thereon.

9. The apparatus of claim 6, wherein the telescopic mechanism includes a mount defining a channel and a lock bar coupled to the locking body and formed for sliding movement through the channel.

10. A bone drilling guide apparatus comprising:

a template including a sliding body and a locking body, the sliding body including an inferior surface, a superior surface, and a channel extending through the inferior surface, first and second drill towers extending between the sliding and locking bodies respectively, the drill towers including at least one drill passage therethrough, and a telescopic mechanism extending between the sliding and locking bodies, the telescopic mechanism including a lock bar coupled to the locking body and extending through the channel, and a lock to engage the lock bar to lock the locking body in a fixed position relative to the sliding body and disengage the lock bar to permit adjustment of the relative position between the locking body and the sliding body.

11. A bone drilling guide apparatus comprising:

a template including a sliding body and a locking body;

first and second drill towers extending from the sliding body and the locking body respectively, the drill towers including at least one drill passage therethrough; and a telescopic mechanism extending between the sliding body and the locking body to permit movement of the template between an expanded position and a retracted position;

the telescopic mechanism including a mount defining a channel and a lock bar coupled to the locking body and formed for sliding movement through the channel;

the telescopic mechanism further including a clip pivotable relative to the mount and formed for engagement with the lock bar to prevent movement of the lock bar relative to the sliding body.

12. A bone drilling guide apparatus comprising:

a template including a sliding body and a locking body, the sliding body including an inferior surface, a superior surface, and a channel extending through the inferior surface;

first and second drill towers extending from the sliding body and the locking body respectively, the drill towers including at least one drill passage therethrough; and a telescopic mechanism extending between the sliding and locking bodies, the telescopic mechanism including a lock bar coupled to the locking body and extending through the channel;

the telescopic mechanism further including a button tower coupled to the sliding body and a shaft extending through the button tower into the channel for engagement with the lock bar.

13. A bone drilling apparatus comprising:

a template including a sliding body and a locking body, the sliding body including an inferior surface, a superior surface, and a channel extending through the inferior surface;

first and second drill towers extending from the sliding and locking bodies respectively, the drill towers including at least one drill passage therethrough; and a telescopic mechanism extending between the sliding and locking bodies, the telescopic mechanism including a lock bar coupled to the locking body and extending through the channel;

the lock bar including lock slots, the telescopic mechanism including a shaft formed for extension into one of the lock slots to hold the lock bar in a fixed position relative to the locking body and the sliding body.

14. A bone drilling guide apparatus comprising:

a template including a sliding body and a locking body, the sliding body including an inferior surface, a superior surface, and a channel extending through the inferior surface;

first and second drill towers extending from the sliding and locking bodies respectively, the drill towers including at least one drill passage therethrough; and a telescopic mechanism extending between the sliding and locking bodies, the telescopic mechanism including a lock bar coupled to the locking body and extending through the channel;

the sliding body including an aperture extending between the superior and inferior surfaces and a secondary channel extending between the aperture and the channel and the telescopic mechanism further including a generally L-shaped clamp that extends through the aperture and the secondary channel and engages the lock bar to hold the lock bar in a fixed position relative to the locking and sliding bodies.

15. The apparatus of claim 14, wherein the lock bar includes a superior side, an inferior side, and lock slots formed in the inferior side and the clamp extends into the lock slots when the lock bar is in the fixed position.

* * * * *